(12) United States Patent
Anseth et al.

(10) Patent No.: US 9,987,393 B2
(45) Date of Patent: Jun. 5, 2018

(54) COVALENTLY CROSS LINKED HYDROGELS AND METHODS OF MAKING AND USING SAME

(71) Applicant: The Regents of the University of Colorado, A Body Corporate, Denver, CO (US)

(72) Inventors: Kristi Anseth, Boulder, CO (US); Ben Fairbanks, Oakleigh South (AU); Christopher Bowman, Boulder, CO (US)

(73) Assignee: THE REGENTS OF THE UNIVERSITY OF COLORADO, A BODY, Denver, CO (US)

( * ) Notice: Subject to any disclaimer, the term of this patent is extended or adjusted under 35 U.S.C. 154(b) by 0 days. days.

(21) Appl. No.: 15/409,392

(22) Filed: Jan. 18, 2017

(65) Prior Publication Data

US 2017/0232143 A1 Aug. 17, 2017

Related U.S. Application Data

(63) Continuation of application No. 13/981,885, filed as application No. PCT/US2012/022920 on Jan. 27, 2012, now abandoned.

(60) Provisional application No. 61/437,435, filed on Jan. 28, 2011.

(51) Int. Cl.

| | |
|---|---|
| *A61L 27/52* | (2006.01) |
| *C08L 101/02* | (2006.01) |
| *C08F 38/00* | (2006.01) |
| *A61L 27/18* | (2006.01) |
| *C08G 75/045* | (2016.01) |
| *A61L 27/54* | (2006.01) |
| *A61L 27/22* | (2006.01) |
| *C08L 81/02* | (2006.01) |
| *C12N 5/00* | (2006.01) |

(52) U.S. Cl.
CPC ............. *A61L 27/18* (2013.01); *A61L 27/22* (2013.01); *A61L 27/52* (2013.01); *A61L 27/54* (2013.01); *C08G 75/045* (2013.01); *C08L 81/02* (2013.01); *C12N 5/0068* (2013.01); *A61L 2430/02* (2013.01); *A61L 2430/06* (2013.01); *A61L 2430/34* (2013.01)

(58) Field of Classification Search
None
See application file for complete search history.

(56) References Cited

U.S. PATENT DOCUMENTS

| | | |
|---|---|---|
| 3,920,877 A | 11/1975 | Barber et al. |
| 4,081,598 A | 3/1978 | Morgan et al. |
| 4,808,638 A | 2/1989 | Steinkraus et al. |
| 4,969,998 A | 11/1990 | Henn |
| 5,177,056 A | 1/1993 | Hilti et al. |
| 5,399,624 A | 3/1995 | Glaser et al. |
| 5,410,016 A | 4/1995 | Hubbell et al. |
| 5,496,872 A | 3/1996 | Constancis et al. |
| 5,730,601 A | 3/1998 | Bowman et al. |
| 5,837,751 A | 11/1998 | Jacobine et al. |
| 5,858,746 A | 1/1999 | Hubbell et al. |
| 6,060,582 A | 5/2000 | Hubbell et al. |
| 6,169,126 B1 | 1/2001 | Szum et al. |
| 7,018,655 B2 | 3/2006 | Lele et al. |
| 7,288,608 B2 | 10/2007 | Bowman et al. |
| 7,744,912 B1 | 6/2010 | Hubbell et al. |
| 7,842,667 B2 | 11/2010 | Seliktar et al. |
| 8,519,086 B2 | 8/2013 | Bowman et al. |
| 8,859,716 B2 | 10/2014 | Bowman et al. |
| 9,631,092 B2 | 4/2017 | Bowman et al. |
| 2002/0004537 A1 | 1/2002 | Krongauz et al. |
| 2002/0076443 A1 | 6/2002 | Stein et al. |
| 2003/0144373 A1* | 7/2003 | Bowman .............. C08G 75/045 522/167 |
| 2004/0086479 A1 | 5/2004 | Grinstaff et al. |
| 2004/0091462 A1 | 5/2004 | Lin et al. |
| 2005/0244393 A1 | 11/2005 | Philippart et al. |
| 2006/0029578 A1 | 2/2006 | Hoemann et al. |
| 2006/0204582 A1 | 9/2006 | Stein et al. |
| 2007/0248567 A1 | 10/2007 | Pathak et al. |
| 2009/0311338 A1 | 12/2009 | Pathak et al. |
| 2009/0324720 A1 | 12/2009 | He et al. |
| 2010/0137510 A1 | 6/2010 | Seliktar et al. |
| 2010/0178355 A1 | 7/2010 | Hoemann et al. |
| 2010/0233246 A1 | 9/2010 | Sehl et al. |

(Continued)

FOREIGN PATENT DOCUMENTS

| | | |
|---|---|---|
| GB | 588018 A | 5/1947 |
| JP | 363-280711 A | 11/1988 |

(Continued)

OTHER PUBLICATIONS

Anderson, S.B. et al. (May 2011). "The Performance of Human Mesenchymal Stem Cells Encapsulated in Cell-Degradable Polymer-peptide Hydrogels," Biomaterials 32:3564-3574.

(Continued)

*Primary Examiner* — Abigail Vanhorn
(74) *Attorney, Agent, or Firm* — Morrison & Foerster LLP

(57) ABSTRACT

A thiol-yne polymeric material and methods for producing said polymers are disclosed. The material is produced by the radically mediated polymerization of monomers having alkyne and thiol functional groups. The alkyne moiety, internal or terminal, may react with one or two thiols. Degradable monomers may be used to form degradable polymers.

21 Claims, 1 Drawing Sheet

(56) References Cited

U.S. PATENT DOCUMENTS

| | | |
|---|---|---|
| 2010/0291357 A1 | 11/2010 | Polizzotti et al. |
| 2010/0304338 A1 | 12/2010 | Cramer et al. |
| 2012/0225101 A1 | 6/2012 | Kao et al. |
| 2012/0202263 A1 | 8/2012 | Blakely et al. |
| 2013/0197189 A1 | 8/2013 | Aimetti et al. |
| 2013/0243878 A1 | 9/2013 | Mariner et al. |
| 2014/0038826 A1 | 2/2014 | Anseth et al. |
| 2014/0039085 A1 | 2/2014 | Bowman et al. |
| 2014/0112960 A1 | 4/2014 | Lin |
| 2014/0273153 A1 | 9/2014 | Kazantsev et al. |
| 2015/0133302 A1 | 5/2015 | Bowman et al. |
| 2016/0068639 A1 | 3/2016 | Bowman et al. |
| 2017/0247541 A1* | 8/2017 | Bowman .............. C08G 75/045 |

FOREIGN PATENT DOCUMENTS

| | | | |
|---|---|---|---|
| WO | WO-2009039307 A2 * | 3/2009 | .............. C08J 3/075 |
| WO | WO-2012/103445 A2 | 8/2012 | |
| WO | WO-2012/103445 A3 | 8/2012 | |
| WO | WO-2013/116791 A1 | 8/2013 | |
| WO | WO-2016/130573 A2 | 8/2016 | |

OTHER PUBLICATIONS

Athanasiou, K.A. et al. (1996). "Sterilization, Toxicity, Biocompatibility and Clinical Applications of Polylactic Acid/Polyglycolic Acid Copolymers," *Biomaterials* 17(2):93-102.

Cadée, J.A. et al. (Jun. 5, 2000). "In Vivo Biocompatibility of Dextran-Based Hydrogels," *J Biomed Mater Res.* 50(3):397-404.

Chalker, J.M. et al. (2009). "Enabling Olefin Metathesis on Proteins: Chemical Methods for Installation of S-Allyl Cysteine," *Chem. Commun., The Royal Society of Chemistry* pp. 3714-3716.

Conte, M.L. et al. (2001). "Multi-Molecule Reaction of Serum Albumin Can Occur Through Thiol-Yne Coupling," *Chemical Communications* 47:11086-11088.

Cramer, N.B. et al. (2003). "Thiol-Ene Photopolymerization Mechanism and Rate Limiting Step Changes for Various Vinyl Functional Group Chemistries," *Macromolecules* 36:7964-7969.

Dondoni, A. et al. (2009). "A New Ligation Strategy for Peptide and Protein Glycosylation: Photoinduced Thiol-Ene Coupling," *Chemistry-A European Journal* 15:11444-11449.

Draye, J.-P. et al. (Sep. 1998). "In Vitro and in Vivo Biocompatibility of Dextran Dialdehyde Cross-linked Gelatin Hydrogel Films," *Biomaterials* 19(18):1677-1687.

European Office Action for EP2822533 dated Jan. 1, 2017, 5 pages.

Fairbanks, B. D. et al. (2009). "Thiol-Yne Photopolymerizations; Novel Mechanism, Kinetics, and Step-Growth Formation of Highly Cross-Linked Networks," *Macromolecules* 42:211-217.

Fairbanks, B.D. et al. (2010) "Reaction Rates and Mechanisms for Radical, Photoinitated Addition of Thiols to Alkynes, and Implications for Thiol-Yne Photopolymerizations and Click Reactions," *Macromolecules* 43:4113-4119.

Final Office Action dated Jun. 5, 2006, for U.S. Appl. No. 10/269,916, filed Oct. 10, 2002, 7 pages.

Final Office Action dated Mar. 10, 2009, for U.S. Appl. No. 11/858,062, filed Sep. 19, 2007, 6 pages.

Final Office Action dated May 31, 2011, for U.S. Appl. No. 12/556,640, filed Sep. 10, 2009, 5 pages.

Final Office Action dated Sep. 14, 2012, for U.S. Appl. No. 12/556,640, filed Sep. 10, 2009, 10 pages.

Final Office Action dated Nov. 30, 2015, for U.S. Appl. No. 13/981,885, filed Oct. 9, 2013, 17 pages.

Final Office Action dated Jan. 29, 2016, for U.S. Appl. No. 14/210,106, filed Mar. 13, 2014, 11 pages.

Final Office Action dated Oct. 3, 2016, for U.S. Appl. No. 13/758,942, filed Feb. 4, 2013, 11 pages.

Floyd, N. et al. (2009). "Thiyl Glycosylation of Olefinic Proteins: S-Linked Glycoconjugate Synthesis", *Angewandte Chemie International Edition* 48:798-7802.

Fu, Y. et al., (Aug. 2011) "In Situ Forming Poly ( Ethylene Glycol)-Based Hydrogels Via Thiol-Maleimide Michael-Type Addition," *J. Biomed. Mater. Res.* 98(2):201-211.

Fu, Y. et al. (Jan. 2012), "3D Cell Entrapment in Crosslinked Thiolated Gelatin-poly(ethylene glycol) Diacrylate Hydrogels," *Biomaterials* 33(1):48-58.

Gallez, B. et al. (Jul. 1998). "Small Particles of Fusinite and Carbohydrate Chars Coated with Aqueous Soluble Polymers: Preparation and Applications for In Vivo EPR Oximetry," *Magn Reson Med.* 40(1):152-159.

Geyer, U. et al. (1994). "Formation, Derivatization and Applications of Bacterial Cellulose," *Int. J. Biol. Macromol.* 16(6):343-347.

Hernandez, K. et al. (2011). "Control of Protein Immobilization: Coupling Immobilization and Site-directed Mutagenesis to Improve biocatalyst or Biosensor Performance" *Enzyme & Microbial Technology* 48:107-122.

Hoyle, C.E. et al. (2004). "Thiol-Enes: Chemistry of the Past with Promise for the Future" *Journal of Polymer Science: Part A: Polymer Chemistry* 42:5301-5338.

International Preliminary Report on Patentability dated Jul. 30, 2013, for PCT Patent Application No. PCT/US2012/022920, filed Jan. 27, 2012, 7 pages.

International Preliminary Report on Patentability dated Aug. 8, 2013 for PCT Patent Application No. PCT/US2012/022920, filed on Jan. 27, 2012, 8 pages.

International search report dated Jan. 3, 2003, for PCT Patent Application No. PCT/US02/32669, filed Oct. 10, 2002, 1 page.

International Search Report and Written Opinion dated Aug. 30, 2012, for PCT Patent Application No. PCT/US2012/022920, Internationally filed on Jan. 27, 2012, 9 pages.

International Search Report dated Apr. 11, 2013 for PCT Patent Application No. PCT/US2013/024520 filed on Feb. 1, 2013, three pages. (5.40).

International Search Report dated Aug. 18, 2016, for PCT Patent Application No. PCT/US2016/17189, Internationally filed on Feb. 9, 2016, 4 pages.

Jain, R.A. (2000). "The Manufacturing Techniques of Various Drug Loaded Biodegradable Poly(lactide-co-glycolide) (PLGA) Devices," *Biomaterials* 21:2475-2490.

Jin, R. et al. (Jun. 2010). "Synthesis and characterization of hyaluronic acid-poly(enthylene glycol) hydrogels via Michael addition: An injectable biomaterial for cartilage repair," *Acta Biomaterialia* 6(6):1968-1977.

Jones, M.W. et al. (2009). "Phosphine-Mediated One-Pot Thiol-Ene "Click" Approach to Polymer-Protein Conjugates," *Chem. Commun.* 5272-5274.

Li, Y. et al., (2012). "Genetically Encoded Alkenyl-Pyrrolysine Analogues for Thiol-Ene Reaction Mediated Site-Specific Protein Labeling" *Chemical Science* 3:2766-2770.

Lin, S.S. et al. (Aug. 30-Sep. 3, 2006). "Controlled Release of PRP-Derived Growth Factors Promotes Osteogenic Differentiation of Human Mesenchymal Stem Cells," *Proceedings of the 28th IEEE EMBS Annual International Conference*, New York, USA, SaA06. 4:4358-4361.

Lin, C.C. et al. (2011) "PEG Hydrogels Formed by Thiol-Ene Photo-Click Chemistry and Their Effect on the Formation and Recovery of Insulin-Secreting Cell Spheroids" *Biomaterials* 32(36):9685-9695.

Lowe, A.B. et al. (2010). "Thiol-yne Click Chemistry: A Powerful and Versatile Methodology for Materials Synthesis," *Journal of Materials Chemistry*, 20:4745-4750.

Maleimide, retrieved from <www.en.wikipedia.org/wiki/Maleimides> on Mar. 3, 2012, 3 pages.

McCall, J.D. et al. (2012) "Thiol-Ene Photopolymerizations Provide a Facile Method to Encapsulate Proteins and Maintain Their Bioactivity", Biomacromolecules, 13:2410-2417.

Moreira, H. et al. (Feb. 2000). "Use of Bioresorbable Membrane (Sodium Hyaluronate + Carboxymethylcellulose) After Controlled Bowel Injuries in a Rabbit Model," *Diseases of the Colon Rectum* 43(2):182-187.

Non Final Office Action dated Dec. 30, 2005, for U.S. Appl. No. 10/269,916, filed Oct. 10, 2002, 6 pages.

(56) References Cited

OTHER PUBLICATIONS

Non Final Office Action dated Aug. 6, 2008, for U.S. Appl. No. 11/858,062, filed Sep. 19, 2007, 6 pages.
Non Final Office Action dated Oct. 25, 2010, for U.S. Appl. No. 12/556,640, filed Sep. 10, 2009, 9 pages.
Non-Final Office Action dated Dec. 31, 2015, for U.S. Appl. No. 13/758,942, filed Feb. 4, 2013, 14 pages.
Non Final Office Action dated Nov. 20, 2013, for U.S. Appl. No. 13/951,268, filed Jul. 25, 2013, 9 pages.
Non-Final Office Action dated Apr. 3, 2015, for U.S. Appl. No. 13/981,885, filed Oct. 9, 2013, 16 pages.
Non-Final Office Action dated Jul. 18, 2016, for U.S. Appl. No. 13/981,885, filed Oct. 9, 2013, 18 pages.
Non-Final Office Action dated Jul. 16, 2015, for U.S. Appl. No. 14/210,106, filed Mar. 13, 2014, 10 pages.
Non-Final Office Action dated Sep. 16, 2016, for U.S. Appl. No. 14/210,106, filed Mar. 13, 2014, 12 pages.
Non-Final Office Action dated May 8, 2015, for U.S. Appl. No. 14/485,490, filed Sep. 12, 2014, 10 pages.
Non-Final Office Action dated May 19, 2016, for U.S. Appl. No. 14/848,141, filed Sep. 8, 2015, 12 pages.
Notice of Allowance dated Dec. 14, 2006, for U.S. Appl. No. 10/269,916, filed Oct. 10, 2002, 6 pages.
Notice of Allowance dated Jun. 19, 2007, for U.S. Appl. No. 10/269,916, filed Oct. 10, 2002, 6 pages.
Notice of Allowance dated Apr. 26, 2013, for U.S. Appl. No. 12/556,640, filed Sep. 10, 2009, 6 pages.
Notice of Allowance dated Jun. 11, 2014, for U.S. Appl. No. 13/951,268, filed Jul. 25, 2013, 13 pages.
Notice of Allowance dated Dec. 16, 2016 for U.S. Appl. No. 14/848,141, filed Sep. 8, 2015, 7 pages.
Qiu, B. et al. (2004). "A hydrogel prepared by in situ cross-linking of a thiol-containing poly(ethylene glycol)-based copolymer: a new biomaterial for protein drug delivery," *Biomaterials* 24:11-18.
Raza, A. et al. (2013). "The Influence of Matrix Degradation and Functional on Cell Survival and Morphogenesis in PEG-Based Hydrogels," Macromolecular Bioscience 13:1048-1058.
Restriction Requirement dated Jul. 13, 2005, for U.S. Appl. No. 10/269,916, filed Oct. 10, 2002. 9 pages.
Restriction Requirement dated Sep. 13, 2005, for U.S. Appl. No. 10/269,916, filed Oct. 10, 2002. 5 pages.
Restriction Requirement dated Aug. 31, 2015 for U.S. Appl. No. 13/758,942, filed Feb. 4, 2013, 8 pages.
Restriction Requirement dated Nov. 20, 2014 for U.S. Appl. No. 13/981,885, filed Oct. 9, 2013, 8 pages.
Restriction Requirement dated Feb. 12, 2015, for U.S. Appl. No. 14/210,106, filed Mar. 13, 2014, 6 pages.

Roberts, J.J. et al. (2013). "Comparison of Photopolymerizable Thiol-ene PEG and Acrylate-based PEG Hydrogels for Cartilage Development," Biomaterials 34(38):9969-9979.
Roskos, K.V. et al. (1995). "Biocompatibility and in Vivo Morphine Diffusion into a Placebo Morphine-triggered Naltrexone Delivery Device in Rabbits," *Biomaterials* 16(16):1235-1239.
Russo, L. et al. (Mar. 2016; e-published on Dec. 9, 2015). "Gelatin Hydrogels via Thiol-ene Chemistry," *Monatshefte Für Chemie* 147(3):587-592.
Supplementary European Search Report dated Dec. 14, 2015, for European Patent Application No. 13743245.6, filed on Feb. 1, 2013, 10 pages.
Veronese, F.M. (2001) "Peptide and Protein PEGylation: A Review of Problems and Solutions", *Biomaterials* 22:405-417.
Wiese, K.G. (1993). "Osmotically Induced Tissue Expansion with Hydrogels: A New Dimension in Tissue Expansion? A Preliminary Report," *Journal of Cranio-Maxillo-Facial Surgery* 21:309-313.
Written Opinion dated Aug. 30, 2012, for PCT Application No. PCT/US2012/022920, filed on Jan. 27, 2012, 6 pages.
Written Opinion dated Apr. 11, 2013 for PCT Patent Application No. PCT/US2013/24520 filed on Feb. 1, 2013, 6 pages.
Written Opinion dated Aug. 18, 2016, for PCT Patent Application No. PCT/US2016/17189, Internationally filed on Feb. 9, 2016, 6 pages.
Wu, J.-T. et al. (2012) "Reactive Polymer Coatings: A General Route t Thiol-ene and Thiol-yne Click Reactions" *Macromol. Rapid Commun.* 33:922-927.
Yan, J. et al. (Oct. 8, 2013). "Growing Hyperbranched Polymers Using Natural Sunlight", *Scientific Reports* 3(2841):1-7.
Lee, S. et al. (2016 ; e-published on Nov. 23, 2015). "Fabrication of PEG-carboxymethylcellulose Hydrogel by Thiol-norbornene Photo-click Chemistry," *International Journal of Biological Macromolecules* 83:1-8.
Sell, S.A. et al. (Dec. 2012, e-published on Sep. 25, 2012) "The Incorporation and Controlled Release of Platlet-Rich Plasma-Derived Biomolecules From Polymeric Tissue Engineering Scaffolds," *Polym. Int.* 61(12):1703-1709.
Xiang, Z. et al. (Sep. 2013; e-published on Aug. 4, 2013). "Adding an Unnatural Covalent Bond to Proteins Through Proximity-enhanced Bioreactivity," *Nature Methods* 10(9):885-888 (also includes the Erratum—Corrected after Print on Nov. 21, 2013).
International Preliminary Report on Patentability dated Aug. 24, 2017, for PCT/US2016/017189, filed on Feb. 9, 2016, eight pages.
U.S. Final Office Action dated Jun. 29, 2017, for U.S. Appl. No. 14/210,106, filed Mar. 13, 2014, 14 pages.
U.S. Notice of Allowance dated Oct. 20, 2017, for U.S. Appl. No. 14/210,106, filed Mar. 13, 2014, 11 pages.
U.S. Appl. No. 15/549,787, filed Aug. 9, 2017 by Kazantsev et al.

\* cited by examiner

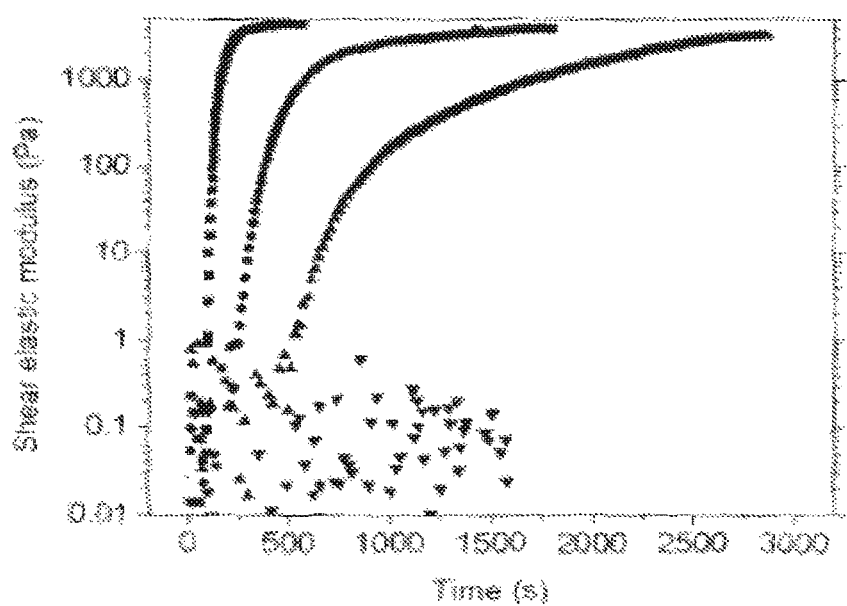

COVALENTLY CROSS LINKED HYDROGELS AND METHODS OF MAKING AND USING SAME

CROSS REFERENCE TO RELATED APPLICATIONS

This application is a Continuation of U.S. patent application No. 13/981,885, which is a National Phase application filed under 35 U.S.C. § 371 of International Application No. PCT/US2012/22920, filed on Jan. 27, 2012, which claims priority from U.S. Provisional Patent Application No. 61/437.435, filed on Jan. 28, 2011,the disclosures of which are hereby incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 70003200401SEQLIST.txt, date recorded: Mar. 15, 2017, size: 1 KB).

BACKGROUND

Materials used for tissue regeneration are designed with precise physical and biological properties. Current methods of producing materials for tissue regeneration are very costly and time consuming. This is due to specialized apparatuses and procedures to make such materials. There is a need for materials used in tissue regeneration that are low in cost, versatile and easily prepared.

SUMMARY

This disclosure provides a composition including a polymer including two or more types of monomers wherein at least a first monomer comprises at least two thiol moieties and at least a second monomer comprises at least one alkyne moiety and wherein the first and second monomers are crosslinked at bonds between the thiol and alkyne moieties. In certain embodiments the first monomer includes at least 2, 3, 4, 5, 6, 7, 8, 9 or 10 thiol moieties. In other embodiments, the second monomer includes at least 1, 2, 3, 4, 5, 6, 7, 8, 9 or 10 alkyne moieties.

In other embodiments, the first and/or second monomer is selected from poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-polypropylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluronic acid, dextran and similar derivatives thereof, heparan sulfate. chondroitin sulfate, heparin, or alginate, and proteins including without limitation gelatin, collagen, albumin, or ovalbumin, or copolymers, or blends thereof. In particularly preferred embodiments, the monomers can be selected from poly(lactic acid) (PLA), polyvinyl alcohol) (PVA), and polyethylene glycol) (PEG). In some embodiments, the monomers are derivatized to include a thiol or alkyne moiety. In one embodiment, one of the monomer is a four arm PEG wherein each PEG arm is chemically modified to include an alkyne at the end of the arm.

In other embodiments, the composition includes a hydrogel. The hydrogel can include more than 50% solvent by weight. In a preferred embodiment, the solvent is water and the hydrogel includes between 50 and 95% water by weight.

In another embodiments, the first or second monomers are degradable. The degradable monomer can be hydrolytically, chemically or enzymatically degradable. In certain embodiments, the first monomer comprises a peptide. Optionally, the peptide can be enzymatically degradable. This enzyme can be a protease. The peptide can he selected from adhesion peptides (such as RGD adhesion sequence), growth factors, hormones, antihormones, signaling compounds, enzymes, serum proteins, albumins, macroglobulins, globulins, agglutinins, lectins, extracellular matrix proteins, antibodies, and antigens.

In certain embodiments, the composition described herein can further include an agent that has a biological function or activity, including pharmaceutically active agents. Peptide agents can be selected from adhesion peptides (such as RGD adhesion sequence), growth factors, hormones, antihormones, signaling compounds, enzymes, serum proteins, albumins, macroglobulins, globulins, agglutinins, lectins, extracellular matrix proteins, antibodies, and antigens. Non-peptide agents that can be incorporated into the polymeric material include analgesics, antipyretics, nonsteriodal anti-inflammatory drugs, antiallergics, antibacterial drugs, anti-anemia drugs, cytotoxic drugs, antihypertensive drugs, dermatological drugs, psychotherapeutic drugs, vitamins, minerals, anorexiants, dietetics, antiadiposity drugs, carbohydrate metabolism drugs, protein metabolism drugs, thyroid drugs, antithyroid drugs, and coenzymes. In certain embodiments, the composition described herein can further include an agricultural chemical. The agricultural chemical can be selected from fungicides, herbicides, fertilizers, pesticides, carbohydrates, nucleic acids, organic molecules, and inorganic biologically active molecules.

With respect to the above two paragraphs, it is not necessary that these agents he covalently attached to the polymer. However, in certain embodiments, these agents may be covalently attached to polymer using the same thiol-yne chemistry. In other embodiments, these agents may be covalently attached using other chemistries.

This disclosure further provides a method for producing the compositions described above including providing the first and second monomers; mixing the first and second monomers with a photoinitiator in solvent; and exposing the first and second monomers and photoinitiator to light. In certain embodiments, the photoinitiator is selected from Irgacure 2959, 184 and 651.

In one embodiment, the light is ultraviolet light. The ultraviolet light can have a wavelength between 300 and 400 nm. In other embodiments, the light can be in the visible or IR spectrum. The exposure to light can last for less than one, two, five or 20 minutes.

In other embodiments, the solvent is present at greater than 50% of the mixture of the first and second monomer, photoinitiator and solvent.

This disclosure further provides a method of culturing cells comprising growing the cells on the compositions described above. In certain embodiments, the cells are mammalian cells. The mammalian cells can be human cells. In other embodiments, the cells are primary cells or stem cells.

The disclosure further provides kits. These kits can include the compositions including two or more types of monomers wherein at least a first monomer comprises at least two thiol moieties and at least a second monomer comprises at least one alkyne moiety and wherein the first and second monomers are crosslinked at bonds between the thiol and alkyne moieties. These kits can also include the monomers and photoinitiator used to produce the compositions described herein. These kits can also include the compositions described herein as well as cells that can be cultured on these compositions as described above.

BRIEF DESCRIPTION OF THE DRAWING

The FIGURE is a line graph showing shear elastic modulus versus time.

DETAILED DESCRIPTION

The present disclosure provides a novel class of scaffolds which are thiol-yne hydrogels. These scaffolds are produced by the radical mediated polymerization of monomers containing alkyne and thiol functional groups. In certain embodiments, the scaffold is a three dimensional polymer matrix.

Thiol-yne polymerizations are radical mediated processes that take place between thiols and alkyne-containing moieties via a sequential propagation/chain-transfer process. In certain embodiments, polymerizations occur between two types of monomer. The first type of monomer is derivatized with thiol groups and the second type of monomer is derivatized with alkyne groups. The thiol monomer can be derivatized with 2, 3, 4, 5, 6, 7, 8, 9, 10 or more thiol groups. The alkyne monomer can be derivatized with 1, 2, 3, 4, 5, 6, 7, 8, 9, 10 or more alkyne groups. For example, in this embodiment, the thiol monomer could have three thiol moieties and the alkyne monomer could have two alkyne moieties. In other embodiments, each thiol-containing component has an average of at least two thiol groups. In this embodiment, because each alkyne functional group is capable of undergoing up to two reactions with thiols, each alkyne-containing component has at least one alkyne functional group, (i.e. the monomer contains one or more triple bonds). Crosslinked gels can be readily formed by increasing the monomer functionality of one or both of the monomers to allow for more than two reactions per monomer.

In one embodiment, these scaffolds may be built upon degradable materials, such as peptides, proteins, and poly (lactic acid) blocks. In another embodiment, they can incorporate chemicals and live cells within the polymer matrix.

In one embodiment, an initiating system is used to generate radicals that initiate polymerization. Radicals may be generated by redox, thermal, enzymatic or photochemical mechanisms.

In one embodiment the initiator is a photoinitiator present in the monomer solution at a concentration of less than 5% by weight and is capable of initiating polymerization upon exposure to UV, visible or infra-Red light at an intensity general ranging from 0.1 to 200 mW/cm$^2$ with both higher and lower light intensities possible.

In a preferred embodiment initiator concentration and light intensity will be sufficient for polymerization to occur, resulting in a crosslinked material, often in less than 20 minutes, preferably polymerization will occur in less than 5 minutes, preferably polymerization will occur in less than 2 minutes, more preferably polymerization will occur in less than 1 minute. Initiators include, but are not limited to Irgacure 2959, 184 and 651.

In an embodiment the initiator will be capable of initiating polymerization in a dilute monomer solution containing more than 50% solvent. Preferably the initiator is a photoinitiator capable of initiating polymerization in the presence of water, and water is preferably used as the solvent. More preferably the photoinitiator will be present in the monomer solution in an amount less than or equal to 0.5%, 1% or 5% by weight and is a water soluble photoinitiator such as but not limited to Irgacure-2959 or water soluble acyl-phosphinate initiator such as but not limited to salts of phenyl-2,4,6-trimethylbenzoylphosphinate.

As mentioned above, the resulting polymer may be crosslinked wherein at least one of the co-monomers can form more than two bonds on average. In specific embodiments, at least one of the monomers contains more than one alkyne functionality or more than two thiol functionalities. Example 4 below demonstrates the ability of the alkyne to react twice with independent thiol functional groups to produce a crosslinked polymer. In one embodiment, the thiol containing monomer contains two thiol groups and the alkyne containing monomer contains 2, 3, 4, 5, 6, 7, 8, 9 or 10 alkyne groups. In another embodiment, the alkyne containing monomer contains 1 alkyne group and the thiol containing monomer contains 3, 4, 5, 6, 7, 8, 9 or 10 thiol groups. In another embodiment, the alkyne containing monomer contains 2 alkyne groups and the thiol containing monomer contains 3, 4 or 8 yne groups. Based on this disclosure, other combinations will be understood by one skilled in the art.

In some embodiments, the monomer is derivatized to include a thiol or alkyne moiety. In preferred embodiments, the core of the monomer structure, to which the reactive yne or thiol moieties are attached, can be selected from one or more of the following: poly(lactic acid) (PLA), polyglycolide (PGA), copolymers of PLA and PGA (PLGA), polyvinyl alcohol) (PVA), polyethylene glycol) (PEG), polyethylene oxide), polyethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, polyvinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluranic acid, dextran and similar derivatives thereof, heparan sulfate, chondroitin sulfate, heparin, or alginate, and proteins including without limitation gelatin, collagen, albumin, or ovalbumin, or copolymers, or blends thereof. In particularly preferred embodiments, the monomers can be selected from poly(lactic acid) (PLA), polyvinyl alcohol) (PVA), and polyethylene glycol) (PEG). PLA monomers provide degradability to the system while PVA and PEG enhance the hydrophilic nature of the hydrogel and provide for the possibility of further derivatization and/or extensive crosslinking. Peptides can also be derivatized with thiol or alkyne groups.

According to the compositions and methods described herein, peptides can be monomers making up the scaffold. These monomers are derivatized with alkyne or thiol groups. Preferably, thiols are included within the peptides through the use of cysteine residues. Peptides can also be covalently attached to the scaffold matrix, but not be either the first or second monomer. In certain embodiments, these peptides can have a biological activity or function. Peptides can also be encapsulated within the matrix but not covalently attached to the matrix. In certain embodiments, these peptides can also have a biological activity or function.

Similarly, other non-peptide agents that have a biological activity or function can also be covalently attached to the scaffold matrix, but not be either the first or second monomer. This attachment can employ the same thol-yne chemistry as is used in the first or second monomer, or could use a different attachment chemistry. Non-peptide agents can also be encapsulated within the matrix but not covalently attached to the matrix.

The resulting polymers may be low density materials, and may be polymerized in the presence of solvent such as but not limited to water. In the case of hydrogels, the resultant hydrogels may contain >95%, >90%, >80%, >70%, >60% or greater than 50% solvent by weight. In some embodiments the solvent might be a mixture of two or more solvents. For certain biomedical applications it may be most desirable for the initial monomer solution to contain 50-95% water by weight.

In some cases, the monomer choice is dependent on the solvent. In other embodiments, the resulting polymers can be swellable in a solvent by selecting co-monomers of a particular chemical nature. For example, In selecting monomers to form a thiol-yne hydrogel in an aqueous environment, it may be desirable to select monomers that will that have a hydrophilic core, such as PEG, PVA, or peptides that incorporate hydrophilic residues. Gels that are compatible with other solvents can be formed using monomers that are compatible with that solvent. As one skilled in the art will recognize, such monomers can be selected from the above mentioned monomers.

In other embodiments, monomers may contain non-hydrophilic elements (other peptides, PLA segments, etc) such that they add functionality and capabilities. PLA segments, attached to a hydrophilic core, for example, will enable the hydrogel to simultaneously swell in the presence of water while being hydrolytically degradable. Peptide sequences can be incorporated for cell signaling, drug delivery, and to impart enzymatic degradability to the hydrogel.

In other embodiments, other vinyl functional monomers (enes, acrylates and methacrylates as examples) may also be included in the polymerizing mixture. For example, (meth) acrylate components, typically incorporated between 10 and 90% of the reacting monomer mixture, can be copolymerized with the thiol and yne monomers to facilitate polymer network structural differences and to change the material properties such as crosslink density, swelling and degradation.

As mentioned above, in some embodiments, degradable monomers may be incorporated in order to form a polymer that is degradable. In one embodiment, the monomers are chemically (for example under acidic or basic conditions) or hydrolytically degradable. For biological applications, it may be desirable to employ enzymatically degradable monomers. For example, monomers can consist of peptides that are cleaved by proteases such as matrix metallo proteases, serine proteases, aspartic acid proteases, threonine proteases, glutamic acid proteases and cysteine proteases. Other biological polymers that may be degraded by other enzymes may also be used.

A wide variety of molecules can be incorporated into the polymeric material through —OH groups or —SH groups including, but not limited to, peptides, proteins, agents that provide a biological activity or function (including pharmacologically active agents), and agricultural chemicals. Alternatively, such molecules can be encapsulated in the polymeric material or reacted to the polymeric material after polymerization in the event such molecules would lose functionality if chemically bound to the polymeric material or if present during the polymerization, respectively. For example, types of proteins that can be incorporated into the polymeric material include adhesion peptides (such as RGD adhesion sequence), growth factors, hormones, antihormones, signaling compounds, enzymes, serum proteins, albumins, macroglobulins, globulins, agglutinins, lectins, extracellular matrix proteins, antibodies, and antigens. Types of pharmacologically active agents that can be incorporated into the polymeric material include analgesics, antipyretics, nonsteriodal antiinflammatory drugs, antiallergics, antibacterial drugs, antianemia drugs, cytotoxic drugs, antihypertensive drugs, dermatological drugs, psychotherapeutic drugs, vitamins, minerals, anorexiants, dietetics, antiadiposity drugs, carbohydrate metabolism drugs, protein metabolism drugs, thyroid drugs, antithyroid drugs, and coenzymes. Types of agricultural chemicals that can be incorporated into the polymeric material include fungicides, herbicides, fertilizers, pesticides, carbohydrates, nucleic acids, organic molecules, and inorganic biologically active molecules.

The monomers can vary in size and number of functional groups depending upon desired properties for the resulting polymeric material. More particularly, the molecular weight for the monomers can range from about 100 DA to about 60000 Da to about 200000 Da. Prior to formation of the polymeric material of the present invention, the monomers may be derivatized to include thiol or alkyne moieties such that those moieties can participate in radical mediated thiol-ene polymerization. Thiolated macromers such as polyethylene glycol) dithiol are available commercially. In another embodiment, cysteine residues in peptides and proteins are used to provide the thiol moiety. The alkyne moieties can be selected from any suitable compound having a carbon-carbon triple bond. For example, the alkyne moiety can be selected from any suitable groups such as hexyne, octyne, hexadiyne, PEG multiyne, and others. Other means for providing thiol moieties and alkynes will be known to those skilled in the art.

The resulting polymers may be formed in the presence of cells and other biological compounds such as proteins and peptides. Furthermore, the monomers may contain hydrophilic and non-hydrophilic regions or elements which add chemical, and/or biological, and/or mechanical functionality.

The resulting polymers can be designed to be degradable if one or more of the co-monomers are chosen to be degradable. As used herein, a polymer is degradable when its rate of degradation is increased by greater than 10% when the polymer is exposed to a degrading agent or process. Degrading agents include chemicals, radiation, heat and enzymes. Degrading processes include photoinitiated chemical processes and mechanical processes.

The polymers described herein can be used as a substrate for the growth of various cell types. These cells can be primary cells or stem cells. These polymers can be used as substrates for cell growth in vitro or in vivo. The polymers described herein can be used for soft tissue regeneration, bone regeneration, cartilage regeneration, stem manufacture and stem cell delivery.

EXAMPLES

Example 1

Synthesis of Alkyne Derivatized PEGs 4-pentynoic acid (1.64 g, 16.7 mmol, Fluka) was added to N,N'-dicyclohexylcarbodiimide (3.44 g, 16.7 mmol, Sigma) and dissolved in minimal dichloromethane (DCM) and stirred overnight under argon. The 4-pentynoic anhydride product was then filtered, concentrated, and added to a solution containing vacuum dried poly(ethylene glycol) (PEG, 5 g, 1.67 mmol, Mn~3000, Fluka), pyridine (1.34 mL, 16.7 mmol, Sigma), 4-dimethylaminopyridine (200 mg, 1.67 mmol, Sigma) in minimal DCM and stirred overnight under argon. The crude product was then concentrated, precipitated in diethyl ether, dissolved in deionized water, dialysed for two days and lyophilized to give the desired product.

Similar methods and reagents can be used to form derivatized PEGs of different molecular weight or with a different number of branches. Other methods for producing alkyne derivatized monomers will be readily understood by one skilled in the art. Alkyne derivatized PEGs are also available from commercials sources.

Example 2

Thiol Containing PEGs and Peptides

Thiol derivatized PEG reagents can be purchased from a number of vendors with a variety of molecular weights. To create a degradable thiol-yne polymer, the peptide sequence KCGGYRGCK (SEQ ID NO: 1) was synthesized using standard peptide synthesis methods. This chymotrypsin sensitive biscysteine peptide provides two thiol moieties and can be cleaved by the protein chymotrypsin.

Methods for preparing other thiol containing monomers will be readily understood by one skilled in the art.

Example 3

Hydrogel Formation 10 kD 4-Arm PEG Thiol (PEG tetrathiol) was mixed with PEG-3K dialkyne such that the thiol to yne ratio was 1:1. To this was added a 0.8% wt. (36 mM) solution of the photoinitiator Irgacure 2959 in water, such that the final formulation was 13.5% PEG. Polymerization is then initiated by irradiation of the mixture at a wavelength between 300-400 nm using a 10 mW/cm$^2$ light source for 1000 seconds.

10 kD 4-Arm PEG Thiol (PEG tetrathiol) was mixed with PEG-3K dialkyne such that the thiol to yne ratio was 2:1. To this was added a 0.8% wt. (36 mM) solution of the photoinitiator Irgacure 2959 in water, such that the final formulation was 13.5% PEG. Polymerization is then initiated by irradiation of the mixture at a wavelength of 300-400 nm using a 10 mW/cm$^2$ light source for 1000 seconds. In this polymerization reaction, the yne moiety reacts twice with thiol contain moieties—first as the original alkyne and subsequently as a vinyl sulfide.

Example 4

Time Course of Photochemical Polymerization of thiol-yne Hydrogels

In situ dynamic photorheometry was used to demonstrate the photochemical curing of thiol-yne hydrogels (all systems were cured with 0.5 wt % Irgacure 2959 and 10 mW/cm$^2$ 365 nm centered UV light). As shown in The FIGURE, the elastic modulus of evolving hydrogel networks was plotted against time. Samples were formulated with 2:1 thiol:alkyne of PEG3400 dithiol and PEG10K tetrayne; 2:1, thiol:alkyne chymotrypsin degradable bicysteine peptide and PEG tetrayne (circle); 1:1 thiol:alkyne chymotrypsin degradable bicysteine peptide and PEG tetrayne (triangle); and PEG terayne alone (inverted triangle).

Example 5

Chymotrypsin Sensitive FRET Substrate

The sequence KKCBK(FAM)GPQGIWGQK(TAMARA)GCKK (SEQ ID NO: 2)was synthesized to yield a biscycteine monomer that generates a FRET signal when cleaved by chymotrypsin. This biscysteine peptide is capable of participating in the thiol-yne polymerization. Cleavage of this peptide by chymotrypsin can be monitored by observing the relative fluorescence when excited with 488 nm light.

Example 6

Formation of Degradable Hydrogels Using the thiol-yne System

Hydrogels were formed as above using the chymotrypsin sensitive biscysteine peptide and a four arm yne derivatized PEG. In addition the above FRET peptide was included into the monomer mixture, thereby incorporating itself in the network architecture. The resulting hydrogels degraded completely within 1 hour when treated with chymotrypsin at 10 mg/ml. Those gels that were not treated with chymotrypsin were stable for longer than 21 days when kept in sterile conditions. Furthermore, the liquid from the degraded hydrogel solution emitted high fluorescence when excited with 488 nm light while an equivalent concentration of the intact FRET substrate emitted little florescence. This indicates that the gel degradation was caused by peptide lysis achieved by the chymotrypsin enzyme (Data shown in Table 1).

TABLE 1

| Fluorescence relative to supernatant from gels not treated with chymotrypsin. | |
|---|---|
| Liquid from non treated gels | 1.0 ± 0.2 |
| Liquid from enzyme treated gels | 32 ± 2 |
| Liquid with equivalent FRET substrate- no enzyme | 3.8 ± 1.2 |

The invention claimed is:

1. A method for producing a composition comprising a biocompatible cross-linked thiol-yne hydrogel, the method comprising:
   (a) providing a first monomer comprising at least two thiol moieties and a second monomer comprising an alkyne moiety;
   (b) mixing the first and second monomers with a photoinitiator in a solvent wherein the solvent is water and is present at greater than 50% of the mixture of the first and second monomers, photoinitiator and solvent; and
   (c) exposing the first and second monomers and photoinitiator to light, thereby producing the composition in less than 20 minutes.

2. The method of claim 1, wherein the photoinitiator is selected from the group consisting of 1-[4-(2-hydroxyethoxy)-phenyl]-2-hydroxy-2-methyl-1-propane-1-one, 1-hydroxy-cyclohexyl-phenyl-ketone and 2,2-dimethoxy-1,2-diphenylethan-1-one.

3. The method of claim 2, wherein the photoinitiator is present in the mixture of the first and second monomers, photoinitiator, and solvent in an amount less than or equal to 0.5% or 1% by weight.

4. The method of claim 1, wherein the light is ultraviolet light.

5. The method of claim 4, wherein the ultraviolet light has a wavelength between 300 and 400 nm.

6. The method of claim 1, wherein the exposure to light lasts for less than two, five or 20 minutes.

7. The method of claim 1, wherein the first monomer comprises two thiol moieties.

8. The method of claim 1, wherein the second monomer comprises at least two alkyne moieties.

9. The method of claim 1, wherein the first monomer comprises a core monomer structure selected from the group consisting of poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses, nucleic acids, polypeptides, polysaccharides, heparan sulfate, chondroitin sulfate, heparin, alginate, copolymers thereof, and blends thereof.

10. The method of claim 1, wherein the second monomer comprises a core monomer structure selected from the group consisting of poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses, nucleic acids, polypeptides, polysaccharides, heparan sulfate, chondroitin sulfate, heparin, alginate, copolymers thereof, and blends thereof.

11. The method of claim 1, wherein the hydrogel comprises between 50 and 95% water by weight.

12. The method of claim 1, wherein the first or second monomers are degradable.

13. The method of claim 12, wherein the degradable monomer is hydrolytically, chemically or enzymatically degradable.

14. The method of claim 1, wherein the first monomer comprises a peptide.

15. The method of claim 14, wherein the peptide is enzymatically degradable.

16. The method of claim 15, wherein the enzyme is a protease.

17. The method of claim 14, wherein the peptide is selected from the group consisting of adhesion peptides, growth factors, hormones, antihormones, signaling compounds, enzymes, serum proteins, albumins, macroglobulins, globulins, agglutinins, lectins, extracellular matrix proteins, antibodies, and antigens.

18. The method of claim 1, further comprising mixing the first and second monomers with an agent that has a biological function or activity.

19. The method of claim 18, wherein the agent is selected from the group consisting of adhesion peptides, growth factors, hormones, antihormones, signaling compounds, enzymes, serum proteins, albumins, macroglobulins, globulins, agglutinins, lectins, extracellular matrix proteins, antibodies, antigens, analgesics, antipyretics, nonsteriodal anti-inflammatory drugs, antiallergics, antibacterial drugs, antianemia drugs, cytotoxic drugs, antihypertensive drugs, dermatological drugs, psychotherapeutic drugs, vitamins, minerals, anorexiants, dietetics, antiadiposity drugs, carbohydrate metabolism drugs, protein metabolism drugs, thyroid drugs, antithyroid drugs, and coenzymes.

20. The method of claim 1, further comprising mixing the first and second monomers with an agricultural chemical.

21. The method of claim 20, wherein the agricultural chemical is selected from the group consisting of fungicides, herbicides, fertilizers, pesticides, carbohydrates, nucleic acids, organic molecules, and inorganic biologically active molecules.

\* \* \* \* \*

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Lys Cys Gly Gly Tyr Arg Gly Cys Lys
1               5

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct

<400> SEQUENCE: 2

Lys Lys Cys Asx Lys Gly Pro Gln Gly Ile Trp Gly Gln Lys Gly Cys
1               5                   10                  15

Lys Lys
```